US006750212B2

(12) United States Patent
Peng et al.

(10) Patent No.: US 6,750,212 B2
(45) Date of Patent: *Jun. 15, 2004

(54) PHOTOCHEMOTHERAPEUTIC COMPOSITIONS

(75) Inventors: Qian Peng, Oslo (NO); Jahn M. Nesland, Oslo (NO); Karl E. Giercksky, Oslo (NO); Johan Moan, Oslo (NO); Trond Warloe, Oslo (NO)

(73) Assignee: PhotoCure AS (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/350,690

(22) Filed: Jul. 9, 1999

(65) Prior Publication Data

US 2002/0061871 A1 May 23, 2002

Related U.S. Application Data

(63) Continuation of application No. PCT/GB98/00058, filed on Jan. 9, 1998.

(30) Foreign Application Priority Data

Jan. 10, 1997 (GB) .............................. 9700396

(51) Int. Cl.$^7$ .............................................. A01N 55/02
(52) U.S. Cl. ....................................................... 514/185
(58) Field of Search ........................ 514/185; 436/518, 436/533, 534

(56) References Cited

U.S. PATENT DOCUMENTS

| 4,575,515 | A |   | 3/1986 | Sandborn |
| 4,925,736 | A | * | 5/1990 | Shikowitz |
| 5,079,262 | A |   | 1/1992 | Kennedy et al. |
| 5,211,938 | A |   | 5/1993 | Kennedy et al. |
| 5,219,878 | A |   | 6/1993 | Ringuet et al. |
| 5,234,940 | A |   | 8/1993 | Kennedy et al. |
| 5,422,093 | A |   | 6/1995 | Kennedy et al. |
| 5,705,518 | A | * | 1/1998 | Richter et al. |
| 5,955,490 | A | * | 9/1999 | Kennedy et al. |

FOREIGN PATENT DOCUMENTS

| DE | 2144382 |   |   | 3/1974 |
| EP | 0 50 036 A2 | * |   | 1/1989 |
| EP | 0350 036 A2 | * |   | 1/1989 |
| EP | 01316179 |   |   | 5/1989 |
| GB | 2058077 A |   |   | 4/1981 |
| JP | 4009360 |   |   | 1/1992 |
| WO | WO 96/28412 |   | * | 1/1989 |
| WO | 91/01727 |   |   | 2/1991 |
| WO | 92/06097 |   |   | 4/1992 |
| WO | 95/07077 |   |   | 3/1995 |
| WO | WO 96/28412 |   | * | 9/1996 |
| WO | 96/28412 |   |   | 9/1996 |

OTHER PUBLICATIONS

Malik et al., J Photochemistry and Photobiology (1995), vol. 28 (3): 213–218. Topical application of 5–aminolevulinic acid, DMSO and EDTA: protoporphyrin IX accumulation in skin and tumours of mice.*
Peng et al., Proc. SPIE—Int. Soc. Opt. Eng. (1996), vol. 2625: 51–57. Effect of desferrioxamine on production of ALA–induced protoporphyrin IX in normal mouse skin.*
Calzavara–Pinton P et al. J of Photochemistry and Photobiology B: Biology, (36): 225–231. Photodynamic therapy with systemic administration of photosensitizers in dermatology, Nov. 1996.*
Berg et al. British J of Cancer (74): 668–697. The influence of iron chelators on the accumulation of protoporphyrin IX in 5–aminoladvulinic acid–treated cells, Sep. 1996.*
Berns M et al. Cancer Research, (42): 2325–2329. In vitro cellular effects of hematoporphyrin derivative, Jun. 1982.*
Calzavara–Pinton P et al. J of Photochemistry and Photobiology B: Biology, (36): 225–231. Photodynamic therapy with systemic administration of photosensitizers in dermatology, Nov. 1996.*
Berg et al. British J of Cancer (74): 688–697. The influence of iron chelators on the accumulation of protoporphyrin IX in 5–aminoladvulinic acid–treated cells, Sep. 1996.*
Berns M et al. Cancer Research, (42): 2325–2329. In vitro cellular effects of hematoporphyrin derivative, Jun. 1982.*
Bedwell, J., et al., "Fluorenscence distribution and photodynamic effect of ALA–induced PP IX in the DMH rat colonic tumor model", *Br. J. Cancer*, vol. 65(6), pp. 818–824, (1992).
Branden, S.V., et al., *J. Chem. Soc. Perkin Trans. 1* (5347132), 1035–1042, (1992).
Brooks, P., et al., "Antiintegrin avb3 blocks human breast cancer growth and angiogenesis in human skin", *J.Clin. Invest.*, vol. 96, pp. 1815–1822, (1995).
Doostdar, H., et al., "The effect of dimethylsulphoxide and 5–amiolaevulinic acid on the activities of cytochrome P450–dependent mixed function oxidase and UPD–glucuronosyl transferase activities in human Hep G2 hepatoma cells.", *Biochemical pharmacology*, vol. 42(6), pp. 1307–1313, (1991).
Dougherty, T.J., "Activated Dyes as Antitumor Agents", *Journal of the National Cancer Institute*, 52, 1333–1336, (Apr. 1974).

(List continued on next page.)

Primary Examiner—Christopher R. Tate
Assistant Examiner—Michele C. Flood
(74) Attorney, Agent, or Firm—Schwegman, Lundberg, Woessner & Kluth, P.A.

(57) ABSTRACT

The invention provides pharmaceutical compositions comprising a protoporphyrin precursor photochemotherapeutic agent together with vascular stroma-localizing photosensitizers, optionally together with at least one surface penetration assisting agent and optionally with one or more chelating agents, and use of the same in treating disorders or abnormalities which are responsive to PDT, preferably exhibiting synergistically enhanced therapy, kits comprising same and methods of therapy and diagnosis.

3 Claims, 8 Drawing Sheets

OTHER PUBLICATIONS

Figure 1:
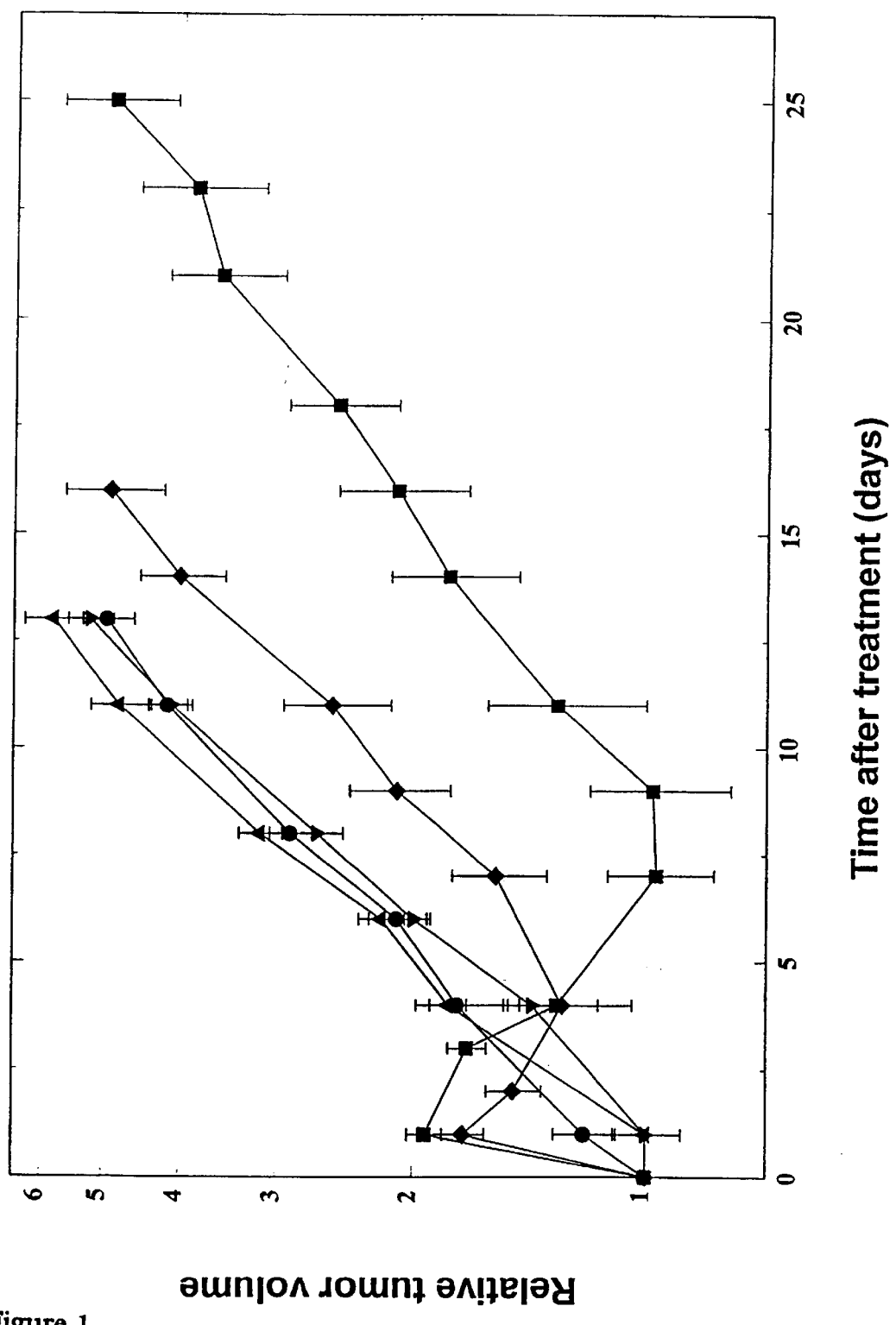

Dougherty, T.J., et al., "Characterization of Intra–Tumoral Porphyrin Following Injection of Hematoporphyrin Derivate or Its Purified Component.", *Photochemistry and Photobiology*, vol. 46 (1), pp. 67–70, (1987).

Gawell, L., et al., *Acta Chem.Scand. EN 43* (5) (651770), 476–480, (1989).

Gawell, L., et al., *Acta Chemica Scandinavica, 43* (5499790), 478–479, (1989).

Gomer, C.J., et al., "Determination of [3H]– and [14C] Hematoporphyrin Derivative Distribution in Malignant and Normal Tissue1", *Cancer Research*, vol. 39, pp. 146–151, (1979).

Hanania, J., et al., "The effect of EDTA and serum on endogenous porphyrin accumulation and photodynamic sentization of human K562 leukemic cells", *Cancer Letters*, vol. 65, pp. 127–131, (1992).

Kelly, J.F., et al., "Hematoporphyrin Derivative: A Possible Aid in the Diagnosis and Therapy of Carcinoma of the Bladder", *The Journal of Urology, 115*, Copyrighted 1976 by The Williams & Wilkins Co., 150–151, (Feb.).

Kessel, D., et al., "Biological and Biophysical Properties of the Tumor–localizing Component of Hematoporphyrin Derivative 1", *Cancer Research*, vol. 45, pp. 3053–3057, (1985).

Kloek, J., et al., "Prodrugs of 5–Aminolevulinic Acid for Photodynamic Therapy", *Photochemistry and Photobiology, 64*(6), 994–1000, (1996).

Lipson, R.L., et al., "The Use of a Derivative of Hematoporphyrin in Tumor Detection", *J. Natl. Cancer Ins.*, vol. 60, pp. 1–10, (1961).

Malik, Z., et al., "Induction of protoporphyrin biosynthesis and photodynamic inactivation of B16 melanoma cells.", *Proceedings of Photodynamic Therapy of Cancer*, vol. 2078, pp. 355–362, (1993).

O'Reilly, M.S., et al., "Angiostatin induces and sustains dormancy of human primary tumors in mice", *Nature Medicine*, vol. 2, pp. 689–692, (1996).

Peng, Q., et al., "5–Aminolevulinic Acid–Based Photodynamic Therapy: Principles and Experimental Research", *Photochemistry and Photobiology*, vol. 65(2), pp. 235–251, (1997).

Peng, Q., et al., "Aluminum Phthalocy Anines with Asymmetrical Lower Sulfonation and with Symmetrical Higher Sulfonation: A Comparison of Localizing and Photosensitizing Mechanism in Human Tumor Lox Xenografts", *Int. J. Cancer*, vol. 46(4), pp. 719–726, (1990).

Peng, Q., et al., "Correlation of distribution of sulphonate aluminum phthalocyanines with their photodynamic effect in tumor and skin of mice bearing CaD2 mammary carcinoma", *Br. J. Cancer*, vol. 72, pp. 565–574, (1995).

Peng, Q., et al., "Correlation of Subcellular and Intratumoral Photosensitizer Localization with Ultrastructural Features After Photodynamic Therapy", *Ultrastructural Pathology*, vol. 20, pp. 109–129, (1996).

Peng, Q., et al., "Uptake, Localization, and Photodynamic Effect of meso–Tetra (hydroxyphenyl) porphine and Its Corresponding Chlorin in Normal Tumor Tissues of Mice Bearing Mammary Carcinoma", *Cancer Research*, vol. 55(12), pp. 2620–2626, (1995).

Qian, P., et al., "A Comparison of Different Photosensitizing Dyes with Respect to Uptake C3H–Tumors and Tissues of Mice", *Cancer Letters, 36*, 1–10, (1987).

Reddi, E., "Transport modalities of phogodynamic agents for tumors", *Spie–int. Soc. Opt. Eng.*, vol. 2078 (Photodynamic therap y of cancer), pp. 246–250, (1994).

Salerni, O.L., et al., *J. Chem. Soc.* (3060978), 1400, (1968).

Salerni, O.L., et al., "Synthesis of Aminolaevulinic Acid Analogues as Potential Antimalarial Agents", *J. Chem. Soc.*, vol. 12, pp. 1399–1401, (1968).

Schulz, G., et al., *Chem. Ber., 113* (2) (5620924), 770–786, (1980).

Schulz, G., et al., *CHBEAM, Chem. Ber., GE, 113* (2) (5633390), 787–790, (1980).

Yamamoto, T., et al., "Significant Inhibition of Endothelial Cell Growth in Tumor Vasculature by an Angiogenesis Inhibitor, TNP–470 (AGM–1470)", *Anticancer Research*, vol. 14, pp. 1–3, (1994).

Zavyalov, S.I., et al., *Bull.Acad. Sci USSR Div. Chem. Sci.* (5991317) 1796–1799, (1987).

\* cited by examiner

PHOTOCHEMOTHERAPEUTIC COMPOSITIONS

CROSS-REFERENCE TO RELATED APPLICATIONS

This application is a continuation of International Patent Application No. PCT/GB98/00058, filed on Jan. 9, 1998, which in turn is an international filing of British Patent Application No. 9700396.6, filed on Jan. 10, 1997, both of which are incorporated herein by reference.

The present invention relates to pharmaceutical compositions for use in the treatment of disorders or abnormalities of the skin and other body surfaces by photochemotherapy.

Abnormalities or disorders, such as neoplasms or psoriatic plaques, of the skin or other epithelial, e.g. mucosal, organs are conventionally treated by surgery, radiotherapy, cryotherapy or chemotherapy. These treatments however, often have significant and serious drawbacks such as toxicity, carcinogenicity, or other unpleasant side effects or general discomfort resulting from the treatment.

Photochemotherapy or photodynamic therapy (PDT) as it is also known, is a recently up-coming technique for the treatment of various abnormalities or disorders of the skin or other epithelial organs, especially cancers or pre-cancerous lesions, as well as certain non-malignant lesions for example skin complaints such as psoriasis. Photochemotherapy involves the application of photosensitizing (photochemotherapeutic) agents to the affected area of the body or systemic application, followed by exposure to photoactivating light in order to activate the photosensitizing agents and convert them into cytotoxic form, whereby the affected cells are killed or their proliferative potential diminished.

A range of photosensitizing agents are known, including notably the psoralens, the porphyrins, the chlorins and the phthalocyanins. Such drugs become toxic when exposed to light.

Photosensitizing drugs may exert their effects by a variety of mechanisms, directly or indirectly. Thus for example, certain photosensitizers become directly toxic when activated by light, whereas others act to generate toxic species, e.g. oxidising agents such as singlet oxygen or other oxygen-derived free radicals, which are extremely destructive to cellular material and biomolecules such as lipids, proteins and nucleic acids. Psoralens are an example of directly acting photosensitizers; upon exposure to light they form adducts and cross-links between the two strands of DNA molecules, thereby inhibiting DNA synthesis. The unfortunate risk with this therapy is that unwanted mutagenic and carcinogenic side effects may occur.

This disadvantage may be avoided by selecting photosensitizers with an alternative, indirect mode of action. For example porphyrins, which act indirectly by generation of toxic oxygen species, have no mutagenic side effects and represent more favourable candidates for photochemotherapy. Porphyrins are naturally occurring precursors in the synthesis of heme. In particular, heme is produced when iron ($Fe^{3+}$) is incorporated in protoporphyrin IX (Pp) by the action of the enzyme ferrochelatase. Pp is an extremely potent photosensitizer, whereas heme has no photosensitizing effect.

One such porphyrin-based drug, PHOTOFRIN® vascular stroma-localizing photosensitizer (Gomer and Dougherty, Cancer Research, 39, p146–151, 1979; originally named Photofrin II) has recently been approved as a photosensitizer in the therapy of certain cancers. PHOTOFRIN® vascular stroma-localizing photosensitizer consists of large oligomers of porphyrin and it does not readily penetrate the skin when applied topically and must therefore be administered systemically. Thus, its main disadvantage is that since it must be administered parenterally, generally intravenously, it causes photosensitization of the skin which may last for several weeks following i.v. injection. Similar problems exist with other porphyrin-based photosensitizers such as the so-called "hematoporphyrin derivative" (Hpd) (Lipson et al., J. Natl. Cancer Ins., 60, p1–10, 1961) which has also been reported for use in cancer photochemotherapy (see for example S. Dougherty., J. Natl. Cancer Ins., 52, p1333, 1974; Kelly and Snell, J. Urol., 115, p150, 1976). Hpd is a complex mixture obtained by treating haematoporphyrin with acetic and sulphuric acids, after which the acetylated product is dissolved with alkali. Clearly, there are disadvantages in using an undefined mixture as a drug. Moreover since Hpd must also be administered by injection, it suffers from the same type of undesirable photosensitization drawback as does PHOTOFRIN®vascular stroma-localizing photosensitizer.

To overcome these problems, precursors of Pp have been investigated for photochemotherapeutic potential. In particular the Pp precursor 5-aminolevulinic acid (ALA) has been investigated as a photochemotherapeutic agent for certain skin cancers. ALA, which is formed from succinyl CoA and glycine in the first step of heme synthesis, is to a limited extent able to penetrate the skin and lead to a localised build-up of Pp; since the action of ferrochelatase (the metallating enzyme) is the rate limiting step in heme synthesis, an excess of ALA leads to accumulation of Pp, the photosensitizing agent. Thus, by applying ALA topically to skin tumours, and then after several hours exposing the tumours to light, a beneficial photochemotherapeutic effect may be obtained (see for example WO91/01727). Since the skin covering basaliomas and squamous cell carcinomas is more readily penetrated by ALA than healthy skin, and since the concentration of ferrochelatase is low in skin tumours, it has been found that topical application of ALA leads to a selectively enhanced production of Pp in tumours.

However, whilst the use of ALA represents a significant advance in the art, photochemotherapy with ALA is not always entirely satisfactory. ALA is not able to penetrate all tumours and other tissues with sufficient efficacy to enable treatment of a wide range of tumours or other conditions and ALA also tends to be unstable in pharmaceutical formulations. Some of these problems may be overcome by using ALA derivatives, for example ester derivatives such as ALA-methylester, ALA-ethylester, ALA-propylester, ALA-hexylester, ALA-heptylester and ALA-octylester and salts thereof as described in our co-pending application WO96/28412.

Like ALA, the ester derivatives exert their effects by enhancing production of Pp; upon delivery to the desired site of action hydrolytic enzymes such as esterases present in the target cells break down the esters into the parent ALA, which then enters the haem synthesis pathway and leads to a build-up of Pp. However, the ester derivatives have a number of advantages over ALA itself. Firstly, they are more lipophilic and better able to penetrate skin and other tissues as compared with ALA; the penetration is both deeper and faster. This is an important advantage, especially for topical administration. Secondly, the esters are better enhancers of Pp production than ALA; Pp production levels following administration of the ALA esters are higher than with ALA alone. Thirdly, the ALA esters demonstrate improved selectivity for the target tissue to be treated, namely the Pp production-enhancing effect is localised to the desired target lesion and does not spread to the surrounding tissues. This is especially evident with tumours. Finally, the esters appear to localise better to the target tissue upon administration. This may be especially important for systemic application, since it means that undesirable photosensitization effects, as reported in the literature for other porphyrin-based photosensitizers, may be reduced or avoided.

Whilst such ALA esters represent a considerable advance in the field of photochemotherapy, not all abnormalities or disorders respond to PDT using known methods to prevent tumour growth and thus there is still a need for better and alternative photochemotherapeutic agents to retard or prevent tumour growth. The present invention thus aims to provide photochemotherapeutic compositions which have an enhanced photochemotherapeutic effect over those described in the prior art.

Studies conducted by the authors have shown that efficient eradication of tumours by PDT requires destruction of both cellular components and also vascular stroma of tumours (Peng & Moan, Br. J. Cancer, 72, p565–574, 1995; Peng et al., Cancer Res., 55, p2620–2626, 1995 and Peng et al., Ultrastructural Pathology, 20, p109–129, 1996). ALA has proven utility in treating tumours and the PpIX synthesized endogenously from ALA localizes within tumour cells. Furthermore, locally applied ALA does not cause skin sensitization and has no mutagenic effect on the DNA of cells. Systemically applied ALA shows no sensitization 24 hours after administration. As mentioned previously however, ALA is not able to penetrate all tumours and has only been found to have good efficacy for the treatment of superficial lesions of the skin with a thickness less than 2–3 mm. No good clinical results have been obtained using topically or systemically administered ALA-PDT on thicker skin lesions or thicker lesions of the aerodigestive tract or other internal hollow organs. PHOTOFRIN® vascular stroma-localizing photosensitizer is known to distribute mainly in vascular stroma of tumours, but as mentioned above, is associated with a prolonged risk of skin photosensitization.

However, it has now surprisingly been found, that the use of a vascular stroma-localizing photosensitizer, e.g. PHOTOFRIN®vascular stroma-localizing photosensitizer, tetra(meso-hydroxyphenyl)chlorin (m-THPC), chlorin e6; aluminium phthalocyanine di-sulfonate or aluminium phthalocyanine tetra-sulfonate in combination with a protoporphyrin precursor photochemotherapeutic agent, e.g. ALA or its methyl or butyl esters, enhances the efficiency of PDT relative to the use of one of the agents alone. A synergistic effect was observed between the vascular stroma-localizing photosensitizer and the protoporphyrin precursor photochemotherapeutic agent, resulting in improved suppression of tumour growth compared to the expected additive effect of the agents alone. This advantageous, synergistic effect was surprisingly observed even when using the vascular stroma-localizing agent at a less than therapeutic dose (sub-therapeutic) which whilst not effective at reducing tumour growth, reduces or avoids the risk of skin photosensitivity. For example, the growth of tumours treated in this way were found to be reduced by using ALA at a therapeutic dose and PHOTOFRIN® vascular stroma-localizing photosensitizer (or m-THPC) at a low non-therapeutic level. The reduction in growth was significantly greater when compared to the additive effects of results obtained using ALA at a therapeutic dose or PHOTOFRIN® vascular stroma-localizing photosensitizer (or m-THPC) at a therapeutic dose. This suggests a hitherto unrecognized synergistic effect between these different types of photochemotherapeutic agents, even at non-therapeutic doses.

The synergistic effect, even at sub-therapeutic levels, has significant clinical implications. Firstly, improved PDT is achieved which is not limited to superficial skin lesions, but may also be used to treat thick skin lesions and superficial lesions of internal hollow organs, and secondly, if sub-therapeutic doses of the vascular stroma-localizing photosensitizer are employed, the skin phototoxicity associated with these agents may be avoided.

In one aspect, the present invention thus provides a pharmaceutical composition for the treatment of disorders or abnormalities of external or internal surfaces of the body which are responsive to photochemotherapy, comprising a protoporphyrin precursor photochemotherapeutic agent together with a vascular stroma-localizing photosensitizer, optionally together with at least one surface penetration assisting agent and optionally with one or more chelating agents. In particular, the therapeutic efficacy of the photochemotherapeutic agents is enhanced, ie. PDT is enhanced relative to the use of one of the agents alone. More particularly, the therapeutic efficacy is synergistically enhanced. In a preferred aspect of the invention, the vascular stroma-localizing photosensitizer is provided at a sub-therapeutic dose.

Alternatively viewed, the invention can be seen to provide the use of a protoporphyrin precursor photochemotherapeutic agent together with a vascular stroma-localizing photosensitizer, optionally together with at least one surface penetration assisting agent and optionally with one or more chelating agents in the preparation of a composition for the treatment of disorders or abnormalities of external or internal surfaces of the body which are responsive to photochemotherapy.

The invention also extends to novel compositions of protoporphyrin precursor photochemotherapeutic agents and vascular stroma-localizing photosensitizers, optionally together with at least one surface penetration assisting agent and optionally with one or more chelating agents.

It will be appreciated that certain vascular stroma-localizing photosensitizers, e.g PHOTOFRIN®vascular stroma-localizing photosensitizer, can not be administered topically, and thus unless both photochemotherapeutic agents of compositions of the invention are administered parenterally, the administration will be by use of separate preparations either administered at the same time or following one another.

Thus, viewed from a further aspect, the invention thus provides a product comprising a protoporphyrin precursor photochemotherapeutic agent and a vascular stroma-localizing photosensitizer, optionally together with at least one surface-penetration assisting agent, and optionally one or more chelating agents as a combined preparation for simultaneous, separate or sequential use in treating disorders or abnormalities of external or internal surfaces of the body which are responsive to photochemotherapy.

Furthermore, the use of a protoporphyrin precursor photochemotherapeutic agent and a vascular stroma-localizing photosensitizer, optionally together with at least one surface-penetration assisting agent, and optionally one or more chelating agents in the preparation of a product for simultaneous, separate or sequential use in treatment of disorders or abnormalities of external or internal surfaces of the body which are responsive to photochemotherapy, forms a further aspect of the invention.

As used herein, "protoporphyrin precursor photochemotherapeutic agents" refers to structural precursors of protoporphyrin and derivatives thereof which function as photochemotherapeutic agents, for example ALA, porphobilinogen or precursors or derivatives thereof, which form a preferred aspect of the invention. Generally such agents localize to cells of the lesion, e.g. a tumour or diseased cell.

"Vascular stroma-localizing agents" refers to agents which generally localize to the vascular stroma after administration. Suitable vascular stroma-localizing agents include:

HpD;

Hematoporphyrines such as PHOTOFRIN® vascular stroma-localizing photosensitizer (Quadra Logic Technologies Inc., Vancouver, Canada) and Hematoporphyrin IX (HpIX);

Photosan III (Seehof Laboratorium GmbH, Seehof, Wesselburenerkoog, Germany);

Clorins such as tetra(m-hydroxyphenyl)chlorins (m-THPC) and their bacteriochlorins (Scotia Pharmaceuticals Ltd, Surrey, UK), mono-L-aspartyl chlorin e6 (NPeG) (Nippon Petrochemical Co., CA, USA), chlorin e6 (Porphyrin Products Inc.), benzoporphyrins (Quadra Logic Technologies Inc., Vancouver, Canada) (e.g. benzoporphyrin derivative monoacid ring A, BPD-MA) and purpurines (PDT Pharmaceuticals Inc., CA, USA) (e.g. tin-ethyl etiopurpurin, SnET2);

phthalocyanines (e.g. zinc-(Quadra Logic Technologies Inc., Vancouver, Canada), some aluminium- or silicon phthalocyanines, which may be sulfonated, in particular sulfonated phthalocyanines such as aluminium phthalocyanine di-sulfonate ($AlPcS_{2a}$) or aluminium phthalocyanine tetra-sulfonate ($AlPcS_4$));

porphycenes;

hypocrellins;

Protoporphyrin IX (PpIX);

Hematoporphyrin di-ethers;

Uroporphyrins;

Coproporphyrins;

Deuteroporphyrin; and

Polyhematoporphyrin (PHP), and precursors and derivatives thereof.

As mentioned previously, PHOTOFRIN® vascular stroma-localizing photosensitizer comprises a mixture of different components and each of these separate components or combinations thereof may be used to provide the vascular stroma-localizing agent.

"Vascular stroma" is intended to signify the vascular connective tissue, matrix and its components and nerves in addition to cells such as macrophages and fibroblasts present in the vascular system and other cells which infiltrate into the stroma. It will be appreciated that the region of localization will depend on the time post-administration at which localization is determined. Thus, photosensitizers which initially localize in cells may relocate to the stroma, and vice versa. For example, aluminium phthalocyanine di-sulfonate localizes initially to the stroma whereas 24–72 hours post-injection the majority of the agent is found in cells.

In general however, vascular stroma-localizing agents are considered to be those present in the stroma in the 24 hours following administration. This may however be manipulated by performing PDT at different times post-administration of the agent such that the agent(s) behaves appropriately as a vascular stroma or lesion-localizing agent at the time of irradiation.

Preferably the protoporphyrin precursor is ALA or a precursor or derivative thereof and the vascular stroma-localizing photosensitizer is a Hematoporphyrin (particularly PHOTOFRIN®vascular stroma-localizing photosensitizer), a chlorin (particularly m-THPC or chlorin e6) or a sulphonated phthalocyanine (particularly aluminium phthalocyanine di-sulfonate or aluminium phthalocyanine tetra-sulfonate).

The term "precursors" as used herein refers to precursors for the agent which are converted metabolically to that agent and are thus essentially equivalent to that agent, e.g. ALA. Thus the term "precursor" covers biological precursors for protoporphyrin in the metabolic pathway for haem biosynthesis. "Derivatives" include pharmaceutically acceptable salts and chemically modified agents, for example esters such as ALA esters as described hereinbefore.

Surface-penetration assisting agents may be used which have a beneficial effect in enhancing the photochemotherapeutic effect. Such agents may be used even when the photochemotherapeutic agents are not administered topically. Dialkylsulphoxides such as dimethylsulphoxide (DMSO) are especially preferred. This is described in detail in WO 95/07077.

The surface-penetration assisting agent may be any of the skin-penetration assisting agents described in the pharmaceutical literature e.g. HPE-101 (available from Hisamitsu), DMSO and other dialkylsulphoxides, in particular n-decylmethyl-sulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 5, p167–177, 1986), and Azone® (Stoughton et al., Drug Dpv. Ind. Pharm., 9, p725–744, 1983), or mixtures thereof.

DMSO however has a number of beneficial effects and is strongly preferred. Thus, in addition to the surface-penetration assisting effect (DMSO is particularly effective in enhancing the depth of penetration of the active agent into the tissue), DMSO has anti-histamine and anti-inflammatory activities, leading to a reduction in pain during the light exposure process. In addition, DMSO has been found to increase the activity of the enzymes ALA-synthase and ALA-dehydrogenase (the enzymes which, respectively, form and condense ALA to porphobilinogen) thereby enhancing the formation of the active form, Pp.

However, in certain conditions such as psoriasis, the lesions are relatively easily penetrated and the penetrating agent may be less beneficial. In some circumstances, for example in the case of skin cancers where the lesions are difficult to penetrate, the surface penetration assisting agent may be applied in a preliminary step, generally at a higher concentration.

Thus, the various active components need not be applied simultaneously within the same composition, but may, according to clinical need, be administered separately and sequentially. Indeed, it has been observed that in many cases a particularly beneficial photochemotherapeutic effect may be obtained by pre-treatment with the surface-penetration assisting agent in a separate step, prior to administration of the photochemotherapeutic agents. Furthermore, in some situations a pre-treatment with the surface-penetration assisting agent, followed by administration of the photochemotherapeutic agent in conjunction with the surface-penetration assisting agent has been found to be beneficial. When a surface-penetration assisting agent is used in pre-treatment this may be used at high concentrations, e.g. up to 100% (w/w). If such a pre-treatment step is employed, the photochemotherapeutic agent may subsequently be administered up to several hours following pre-treatment e.g. at an interval of 5–60 minutes following pre-treatment.

Malik et al in Proceedings of Photodynamic Therapy of Cancer, 2078, p355–362, 1993, described in vitro studies of the effects of ALA, on induction of protoporphyrin biosynthesis, and subsequent killing by photodestruction, of B16 melanoma cells in culture, which had previously been incubated with DMSO as differentiation inducer and/or allyl-isopropyl-acetamide as porphyrogenic agent, to increase endogenous porphyrin levels prior to incubation with the ALA.

Doodstar et al in Biochemical Pharmacology, 42(6), p1307–1303, 1991, describe an investigation into the effects of culture conditions on hepatocytes in culture, and in particular the effects of ALA and DMSO, alone or in combination, on increasing the activities of cytochrome P450-dependent mixed function oxidase and UDP-glucuronosyl transferase, by increasing intracellular haem concentrations, in hepatocyte cells in culture.

Chelating agents are optionally contained in the pharmaceutical composition or product of the invention. Such agents may be useful for two effects, firstly to enhance the stability of the protoporphyrin precursor photochemotherapeutic agent, e.g. ALA and secondly to enhance accumulation of Pp. The latter effect is achieved by the chelation of iron, thereby preventing the inactivating action of the enzyme ferrochelatase in incorporating the metal into Pp, leading to Pp build-up. The photosensitizing effect is thus enhanced.

Hanania et al in Cancer Letters, 65, p127–131, 1992 propose the use of ALA in combination with-chelating agents in photochemotherapy of topically treated tumours.

Aminopolycarboxylic acid chelating agents are particularly suitable for use in this regard, including any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA, DOTA and 1,10-phenanthroline. EDTA is preferred, especially for the stabilisation of ALA. To achieve the iron-chelating effect, desferrioxamine and other siderophores may also be used, e.g. in conjunction with aminopolycarboxylic acid chelating agents such as EDTA.

The compositions of the invention or used according to the invention may additionally be formulated and/or administered with other agents, to improve the efficacy of PDT. Thus for example, angiogenesis inhibitors (anti-angiogenic drugs) which have been found to be useful for treating tumours (O'Reilly et al., Nature Medicine, 2, p689–692, 1996; Yamamoto et al., Anticancer Research, 14, p1–4, 1994; and Brooks et al., J. Clin. Invest., 96, p1815–1822, 1995) may be used together with compositions of the invention in PDT to further damage the vascular system of the tumour. Angiogenesis inhibitors which may be used include TNP-470 (AGM-1470, a synthetic analogue of a fungal secretion product called fumagillin; Takeda Chemical Industries Ltd., Osaka, Japan), angiostatin (Surgical Research Lab. at Children's Hospital Medical Center of Harvard Medical School) and integrin $\alpha_v\beta_3$ antagonists (e.g. monoclonal antibody to intefrin $\alpha_v\beta_3$, The Scripps Research Institute, LaJolla, Calif.).

Alternatively, or additionally, immunotherapy agents (e.g. antibodies or effectors such as macrophage activating factor) or chemotherapy agents may be used to improve PDT according to the invention. Administration of these supplementary agents should be performed in terms of route, concentration and formulation, according to known methods for using these agents. These additional agents may be administered before, after or during PDT, depending on their function. For example, angiogenesis inhibitors may be added 5–10 days after PDT to prevent tumour regrowth.

Glucose has also been found to assist PDT when applied either topically or systemically. Although not wishing to be bound by theory, it appears that administration of glucose results in a lowering of pH which increases the hydrophobic properties of protoporphyrins such that they can penetrate cells more easily. When topical administration is contemplated, conveniently the formulation, e.g. a cream, may contain 0.01 to 10% glucose (w/w).

A preferred composition or product according to the invention, comprises ALA or a precursor or derivative thereof, PHOTOFRIN®vascular stroma-localizing photosensitizer, DMSO, EDTA and desferrioxamine.

As mentioned above, a synergistic effect has been observed, between the protoporphyrin precursor and the vascular stroma-localising photochemotherapeutic agent, whereby the efficiency of PDT is enhanced. Thus, this enables sub-therapeutic dosages of the photochemotherapeutic agent to be used ie. dosages which, were the individual photochemotherapeutic-agent to be administered on its own, would not suffice-to achieve a beneficial photochemotherapeutic effect.

It has in particular been found that beneficial results may be obtained using the protoporphyrin precursor agent, preferably ALA or a derivative thereof, at a therapeutic dose range, standard for PDT using such a photochemotherapeutic agent solely, in conjunction with a sub-therapeutic dose of the vascular stroma-localising agent, preferably PHOTOFRIN®vascular stroma-localizing photosensitizer.

The concentration of the protoporphyrin precursor photochemotherapeutic agent, e.g. ALA in the composition is conveniently in the range 1 to 40%, e.g. 2 to 25, preferably 5 to 20%; the concentration of the vascular stroma-localizing photosensitizer, e.g. PHOTOFRIN® vascular stroma-localizing photosensitizer is conveniently in the range 0.1 to 1% or m-THPC is conveniently in the range 0.01–10%, the concentration of chelating agent is preferably in the range 1 to 20% e.g. about 2 to 10%, e.g. 2.5%; the concentration of surface penetration assisting agent, e.g. DMSO, is preferably in the range 2 to 50% e.g. about 10%. All percentages stated above are by weight. The concentration of agent which is required depends on the particular agent which is used and clearly should be modified as appropriate according to information and techniques known in the art. Furthermore, it will be appreciated that the concentration used depends on the method of application and on the time for which the composition is applied. However, as mentioned above, where the surface penetration assisting agent is administered separately in a preliminary step, it may be applied at higher concentrations, even up to 100%. Compositions of the invention may be administered exclusively topically (by application to internal or external surfaces using for example a cream, instillation, local internal administration/injection or inhalation) or systemically (e.g. orally or by intravenous injection) or by a combination of these methods in which one or more components of the composition is administered topically and the other components are administered systemically.

The total dosage of the vascular stroma-localizing photosensitizer administered, e.g. by intravenous administration is preferably in the range of 0.01 to 10 mg/kg body weight, for example for PHOTOFRIN® vascular stroma-localizing photosensitizer preferably 0.01 to 1 mg/kg body weight (sub-therapeutic dose) or for m-THPC preferably 0.01 to 0.2 mg/kg body weight and for the protoporphyrin precursor photochemotherapeutic agent in the range of 1 to 500 mg/kg, e.g. 1 to 250 mg/kg, for example for ALA in the range 1 to 250 mg/kg, preferably 20 to 70 mg/kg body weight.

It will be appreciated that the dosage required depends on the mode and route of administration, the agent employed and the lesion to be treated. Whilst sub-therapeutic doses of the vascular stroma-localizing photochemotherapeutic agent are preferred, this may be increased if for example a large thick lesion or a difficult type of disease (e.g. melanoma) is to be treated. The observed synergistic effect allows the levels of both the vascular stroma-localizing agent and the protoporphyrin precursor agent to be reduced below normal therapeutic levels.

Alternatively viewed, this aspect of the invention also provides a kit for use in photochemotherapy of disorders or abnormalities of external or internal surfaces of the body comprising:
a) a first container containing a protoporphyrin precursor photochemotherapeutic agent, e.g. ALA or a precursor or derivative thereof;
b) a second container containing a vascular stroma-localizing photosensitizer, e.g. PHOTOFRIN® vascular stroma-localizing photosensitizer or m-THPC; and optionally
c) at least one surface-penetrating agent contained within said first or second container or in a third container; and/or
d) one or more chelating agents contained either within said first, second or third container or in a fourth container;

wherein said first or second container may be absent and the agent or photosensitizer of a) or b) above is present in one of the other containers present in the kit.

Additional components of the kit may also be provided such as angiogenesis inhibitors or glucose as mentioned hereinbefore.

The abnormalities and disorders which may be treated according to the present invention include any malignant, pre-malignant and non-malignant abnormalities or disorders responsive to photochemotherapy e.g. tumours, dysplasia or other growths, non-malignant gynaecological diseases such as menorrhagia, endometriosis and ectopic pregnancy, skin disorders such as psoriasis, actinic keratoses and acne, skin abrasions, and other diseases or infections e.g. bacterial, viral or fungal infections, for example Herpes virus infections. The invention is particularly suited to the treatment of diseases, disorders or abnormalities where discrete lesions are formed (lesions is used here in a broad sense to include tumours and the like). However, the methods of the invention may also be used to treat abnormalities and disorders not characterized by a lesion but displaying discrete separable entities which characterize that disease, for example, abnormalities in the blood or bone marrow indicative of diseases of said blood or marrow or indicative of a disease or disorder located elsewhere in the body which additionally may result in the presence of abnormalities in the blood or marrow, e.g circulating transformed cells.

The internal and external body surfaces which may be treated according to the invention include the skin and all other epithelial and serosal surfaces, including for example mucosa, the linings of organs e.g. the respiratory, gastro-intestinal and genito-urinary tracts, and glands with ducts which empty onto such surfaces (e.g. liver, sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumours such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumours in solid tissues that can be made accessible to photoactivating light e.g. either directly, at time of surgery, or via an optical fibre inserted through a needle.

The compositions of the invention may be formulated in conventional manner optionally with one or more physiologically acceptable carriers or excipients, according to techniques well known in the art. Topical compositions are preferred except when a single composition according to the invention is prepared and a topical composition is not suitable for administration of an agent, e.g. PHOTOFRIN® vascular stroma-localizing photosensitizer in which case systemic application, at least of that agent, will be necessary. Topical compositions include gels, creams, ointments, sprays, lotions, salves, sticks, soaps, powders, pessaries, aerosols, drops and any of the other conventional pharmaceutical forms in the art.

Ointments and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops may be formulated with an aqueous or non-aqueous base also comprising one or more dispersing, solubilising or suspending agents. Aerosol sprays are conveniently delivered from pressurised packs, with the use of a suitable propellant.

Alternatively, the surface penetration assisting agent is applied topically in a separate step, and the vascular stroma-localizing photosensitizer, e.g. PHOTOFRIN® vascular stroma-localizing photosensitizer and protoporphyrin precursor photochemotherapeutic agent, e.g. ALA, optionally together or separately with one or more chelating agents may be administered by an alternative route e.g. orally or parenterally for example by intradermal, subcutaneous, intraperitoneal or intravenous injection. Alternative pharmaceutical forms thus include plain or coated tablets, capsules, suspensions and solutions containing the active components optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

Following administration to the surface or systemic administration, or both, the area treated is exposed to light to achieve the photo-chemotherapeutic effect. This can generally be in the order of a few minutes to 96 hours, preferably 15 minutes to 3 hours. The length of time before light administration is also dependant on the mode of administration, and also the dose and particular agent employed.

The irradiation will in general be applied at a dose level of 10 to 250 Joules/cm$^2$ with an intensity of 20–200 mW/cm$^2$ when a laser is used or a dose of 10–540 J/cm$^2$ with an intensity of 50–300 mW/cm$^2$ when a lamp is applied. At 100 Joules/cm$^2$, penetration of the radiation is found to be relatively deep. Irradiation is preferably performed for 5 to 30 minutes, preferably for 15 minutes. A single irradiation may be used or alternatively a light split dose in which the light dose is delivered in two fractions, e.g. a few minutes to a few hours between irradiations, may be used.

The wavelength of light used for irradiation may be selected to achieve a more efficacious photochemotherapeutic effect. Conventionally, when porphyrins are used in photochemotherapy they are irradiated with light at about the absorption maximum of the porphyrin. Thus, for example in the case of the prior art use of ALA in photochemotherapy of skin cancer, wavelengths in the region 350–640 nm, preferably 610–635 nm were employed. However, by selecting a broad range of wavelengths for irradiation, extending beyond the absorption maximum of the porphyrin, the photosensitizing effect may be enhanced. Whilst not wishing to be bound by theory, this is thought to be due to the fact that when Pp, and other porphyrins, are exposed to light having wavelengths within its absorption spectrum, it is degraded into various photo-products including in particular photoprotoporphyrin (PPp). PPp is a chlorin and has a considerable photo-sensitizing effect; its absorption spectrum stretches out to longer wavelengths beyond the wavelengths at which Pp absorbs ie. up to almost 700 nm (Pp absorbs almost no light above 650 nm). Other agents have been identified for use in PDT which absorb light of even higher wavelengths. Thus in conventional photochemotherapy, the wavelengths used do not excite PPp and hence do not obtain the benefit of its additional photosensitizing effect. Irradiation with wavelengths of light in the range 350–900 nm has been found to be particularly effective although this depends on the agent which is employed. It is particularly important to include the wavelengths between 600 and 700 nm, especially between 630 and 690 nm, specifically the range 630 to 670 nm.

A further aspect of the invention thus provides a method of photochemotherapeutic treatment of disorders or abnormalities of external or internal surfaces of the body, comprising administering to the affected surfaces, a composition or product as hereinbefore defined, and exposing said surfaces to light, preferably to light in the wavelength region 350–900 nm. Alternatively however a light of a narrow wavelength may be used, e.g. when a laser is used, light at a wavelength around 630 nm may be used.

Methods for irradiation of different areas of the body, e.g. by lamps or lasers are well known in the art (see for example Van den Bergh, Chemistry in Britain, May 1986 p. 430–439).

It will be appreciated that the method of therapy using compounds of the invention inevitably involves the fluorescence of the disorder or abnormality to be treated. Whilst the intensity of this fluorescence may be used to eliminate abnormal cells, the localization of the fluorescence may be used to visualize the size, extent and situation of the abnormality or disorder. This is made possible through the ability of the agents used in accordance with the invention to preferentially localize to non-normal tissue.

The abnormality or disorder thus identified or confirmed at the site of investigation may then be treated through alternative therapeutic techniques e.g. surgical or chemical treatment, or by the method of therapy of the invention by continued build up of fluorescence or through further application of compounds of the invention at the appropriate site.

It will be appreciated that diagnostic techniques may require lower levels of fluorescence for visualization than used in therapeutic treatments. Thus, generally, concentration ranges of 1 to 50% e.g. 1–5% (w/w) are suitable. Sites, methods and modes of administration have been considered before with regard to the therapeutic uses and are applicable also to diagnostic uses described here. The compounds of the invention may also be used for in vitro and in vivo diagnostic techniques, for example for examination of the cells contained in body fluids. The higher fluorescence associated with non-normal tissue may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, stools, spinal fluid etc. Tissue samples or preparations may also be evaluated, for example biopsy tissue or bone marrow samples. The present invention thus extends to the use of compounds of the invention, or salts thereof for diagnosis according to the aforementioned methods for photochemotherapy, and products and kits for performing said diagnosis.

A further aspect of the invention relates to a method of in vitro diagnosis, of abnormalities or disorders by assaying a sample of body fluid or tissue of a patient, said method comprising at least the following steps:

i) admixing said body fluid or tissue with a compound as described hereinbefore, ii) exposing said mixture to light, iii) ascertaining the level of fluorescence, and iv) comparing the level of fluorescence to control levels.

Figure 2:
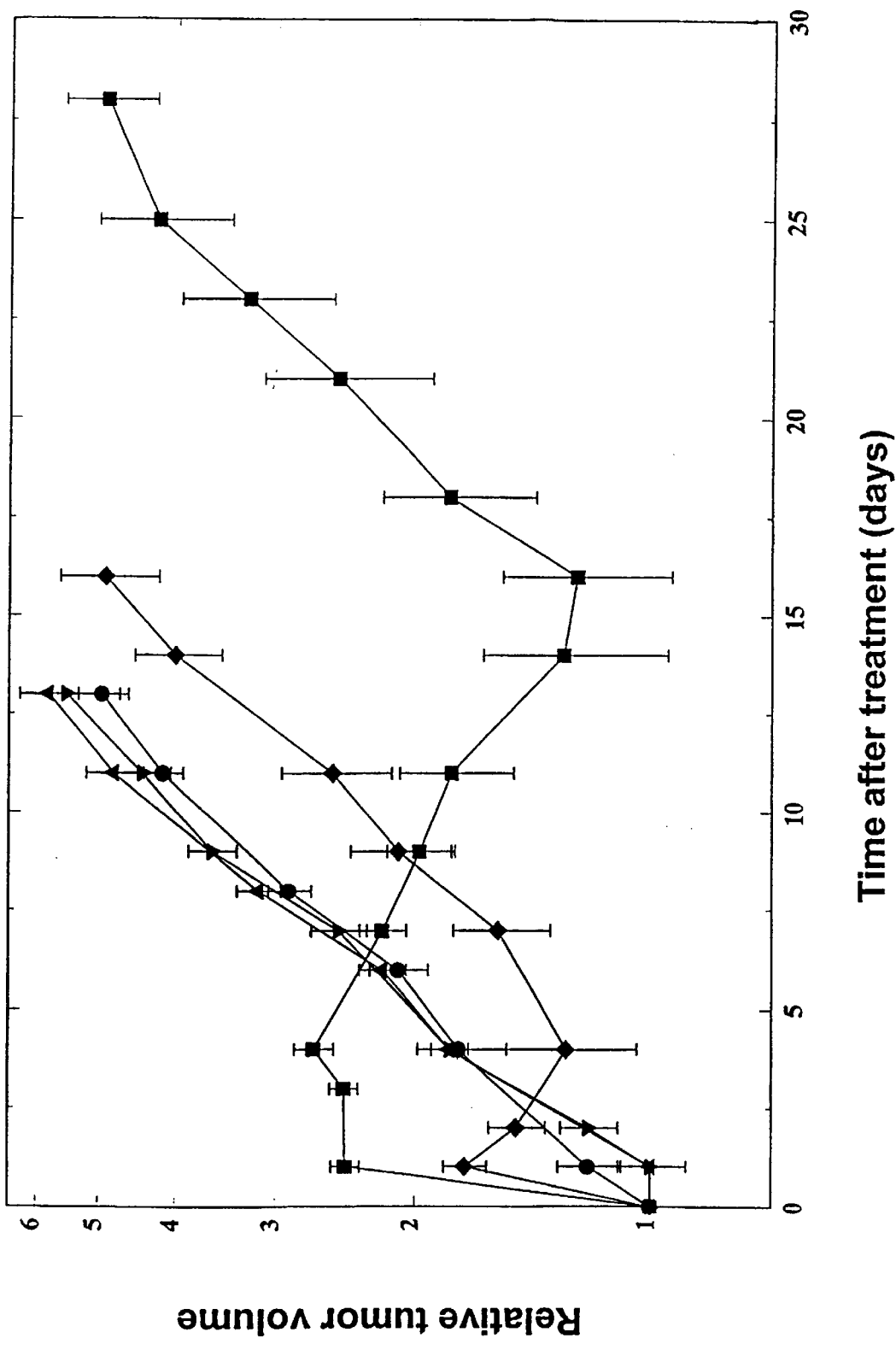
Figure 3:

The invention will now be described in more detail in the following non-limiting Examples, with reference to the drawings in which:

FIG. 1 is a graph showing the averaged results for growth curves of WiDr human colonic carcinoma transplanted subcutaneously into nude mice given intravenous injections of PHOTOFRIN® vascular stroma-localizing photosensitizer and/or intraperitoneal administration of ALA, followed, 3 hours later, by laser light irradiation (632 nm, 150 mW/cm$^2$ for 15 min) ● Control (no drug, no light); ▲ Control (light only); ◆ ALA 250 mg/kg, irradiation after 3 hours; ▼ PHOTOFRIN® vascular stroma-localizing photosensitizer 1 mg/kg, irradiation after 3 hours; ■ ALA 250 mg/kg and PHOTOFRIN® vascular stroma-localizing photosensitizer 1 mg/kg, irradiation after 3 hours; abscissa shows days after treatment; ordinate shows relative tumour volume. Bars indicated standard error of mean (SEM) based on at least 3 animals in each group;

FIG. 2 is a graph showing the averaged results for growth curves of WiDr human colonic carcinoma transplanted subcutaneously into nude mice given intravenous injections of m-THPC and/or intraperitoneal administration of ALA, followed, 3 hours later, by laser light irradiation (632 nm, 150 mW/cm$^2$ for 15 min). ● Control (no drug, no light); ▲ Control (light only); ◆ ALA 250 mg/kg, irradiation after 3 hours; ▼ m-THPC 75 μg/kg, irradiation after 3 hours; ■ ALA 250 mg/kg and m-THPC 75 μg/kg, irradiation after 3 hours; abscissa shows days after treatment; ordinate shows relative tumour volume. Bars indicated standard error of mean (SEM) based on at least 3 animals in each group;

FIG. 3—Fluorescence photomicrographs of human rectal papillary villous adenomas from a 75-year old male (A) and an 87-year old female (B), sampled 44 hours after i.v. injection of 2 mg/kg PHOTOFRIN® vascular stroma-localizing photosensitizer (A) and 4.5 hours after oral administration of 60 mg/kg ALA (B).

Figure 4:
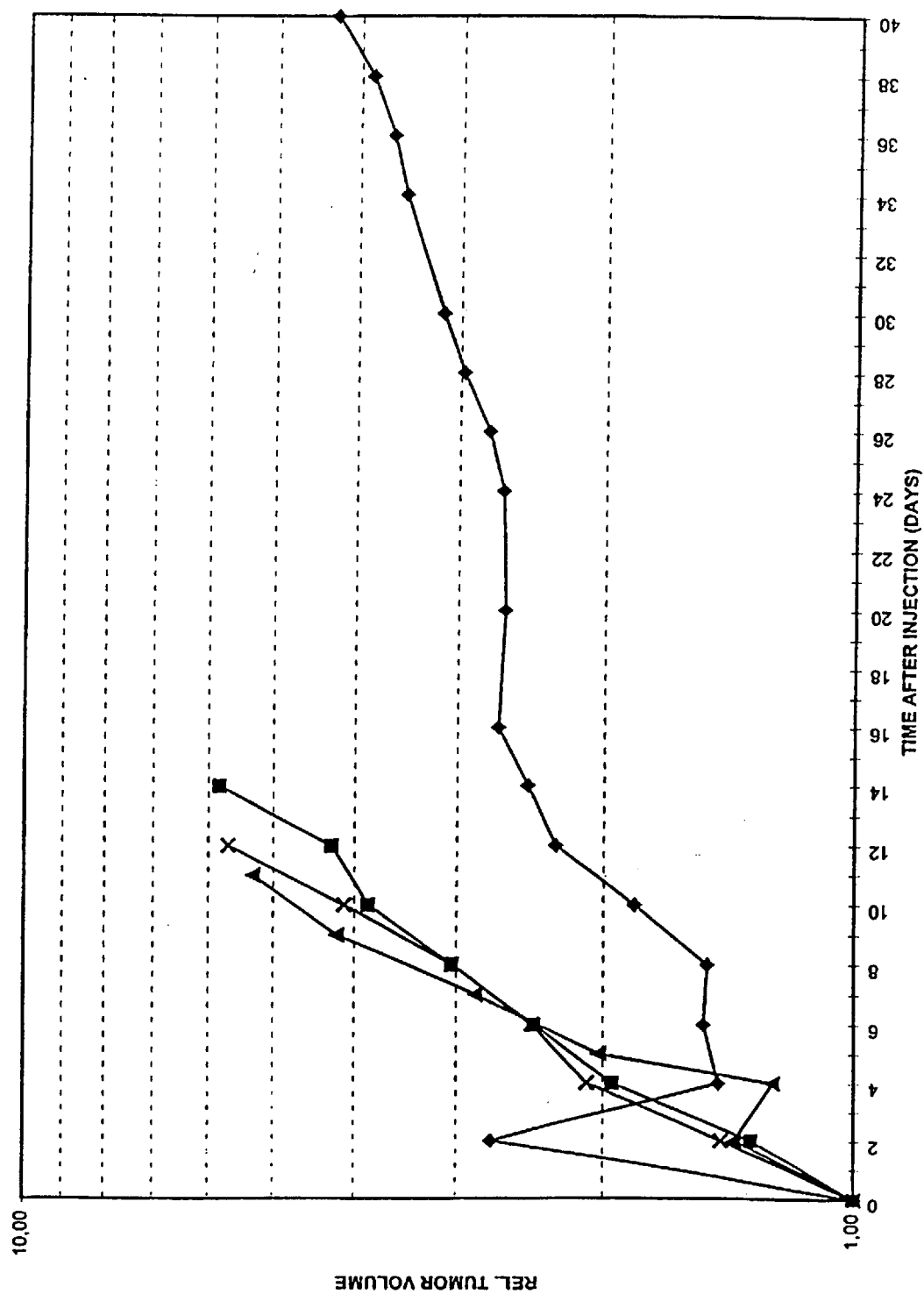
Figure 5:
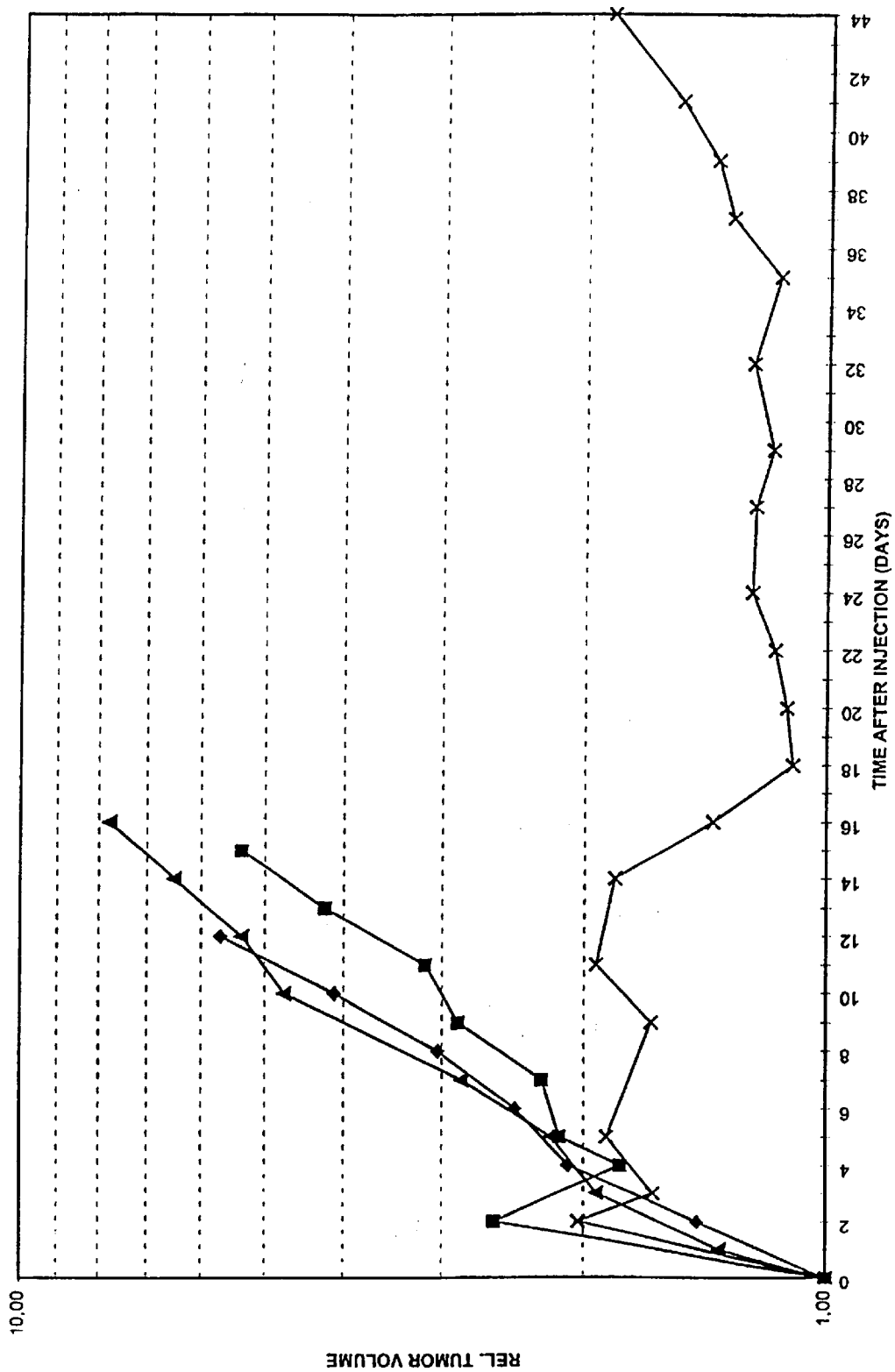
Figure 6:
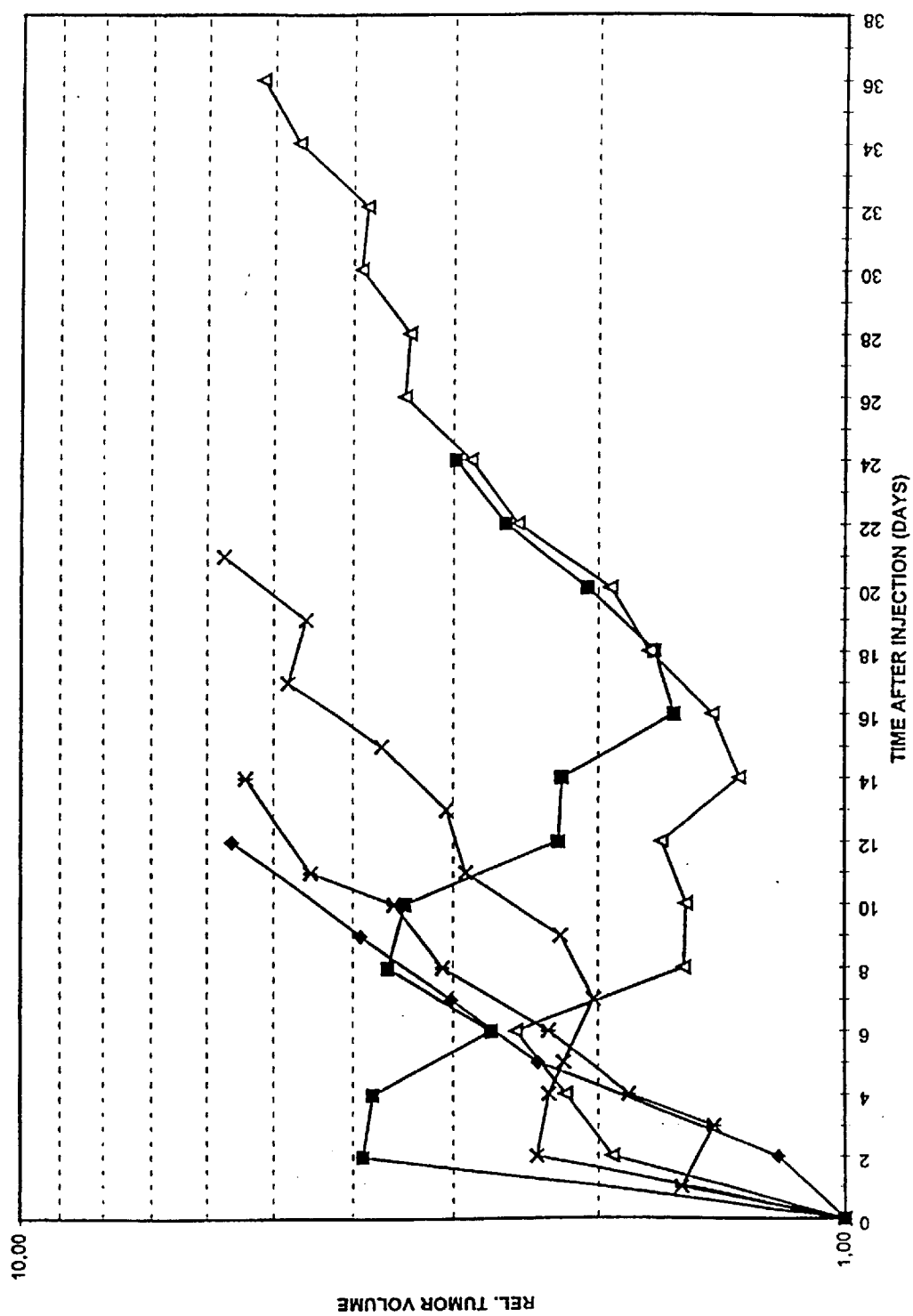
Figure 7:
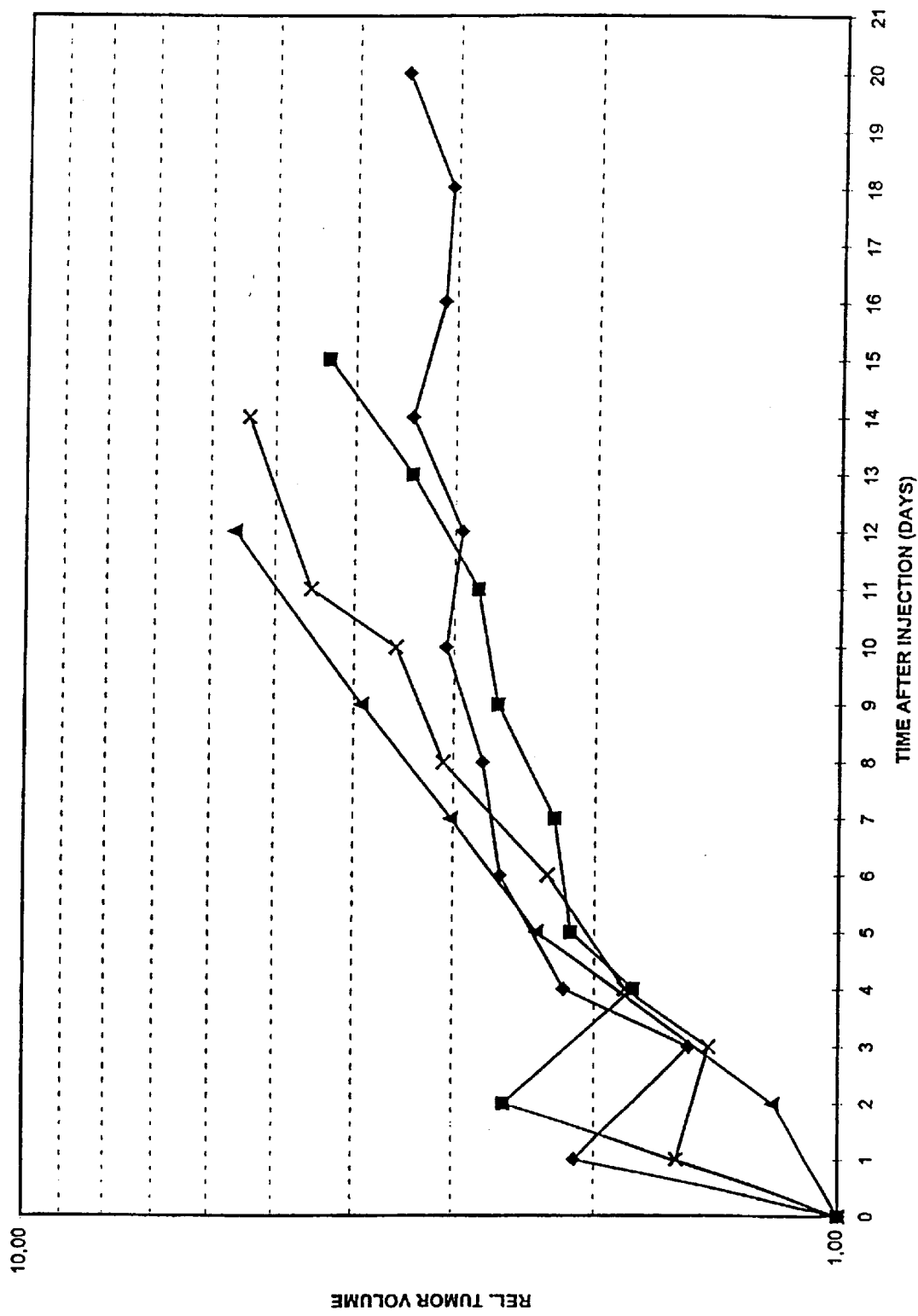
Figure 8:
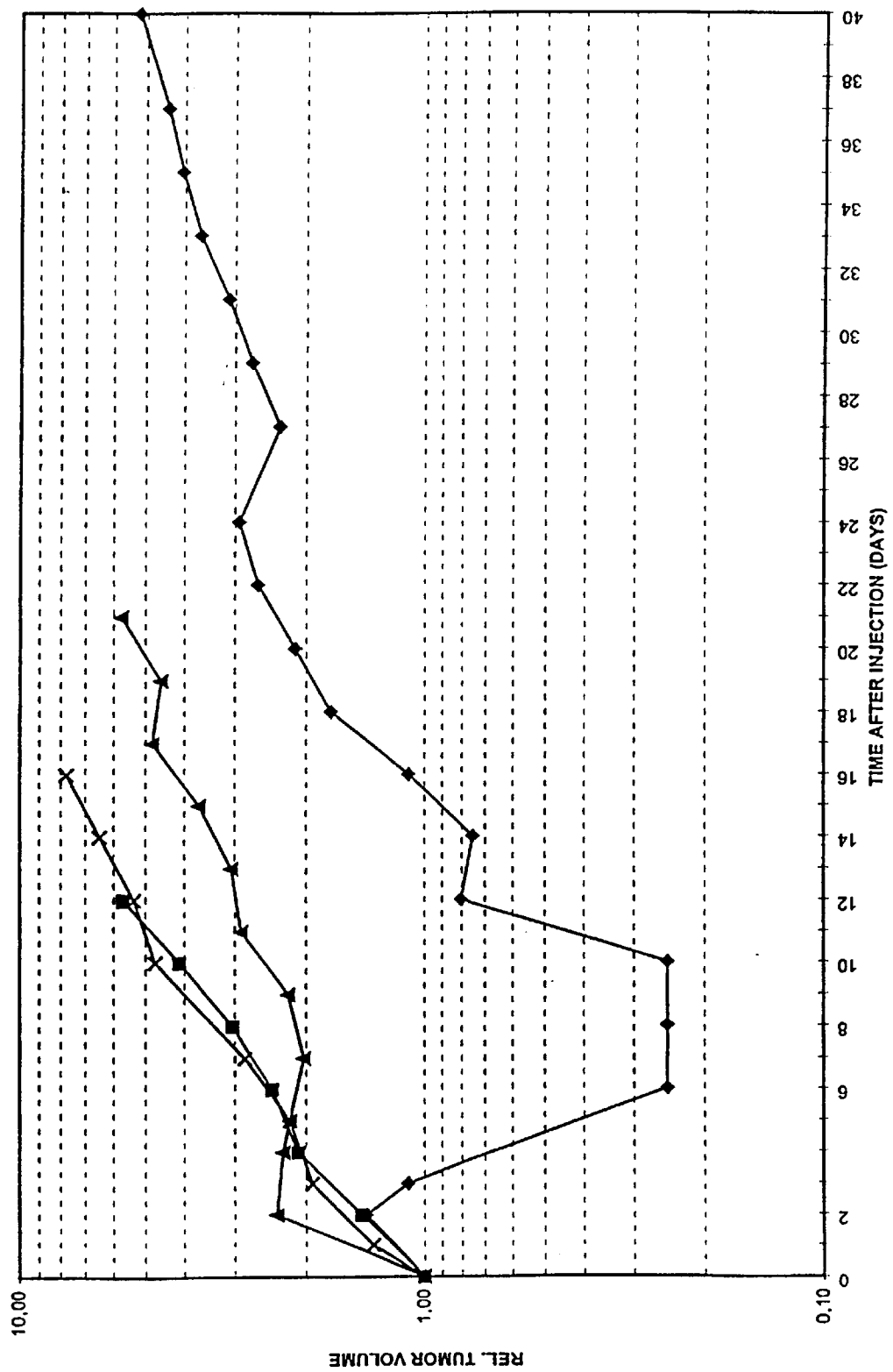

FIG. 4 is as FIG. 1 in which intravenous injections of chlorin e6 and/or intraperitoneal administrations of ALA are made, followed, 1 hour later by lamp irradiation. × Control; ▲ ALA 250 mg/kg; ■ chlorin e6 1 mg/kg; ♦ ALA 250 mg/kg and chlorin e6 1 mg/kg. The abscissa shows days after treatment; ordinate shows relative tumour volume;

FIG. 5 is as FIG. 1 in which intravenous injections of $AlPcS_{2a}$ and/or intraperitoneal administrations of 5-ALA methyl ester are made, followed 1 hour later by lamp irradiation. ♦ Control; ■ $AlPcS_{2a}$ 1 mg/kg; ▲ 5-ALA methyl ester 273 mg/kg; × 5-ALA methyl ester 273 mg/kg and $AlPcS_{2a}$ 1 mg/kg. The abscissa shows days after treatment; ordinate shows relative tumour volume;

FIG. 6 is as FIG. 1 in which intravenous injections of $AlPcS_4$ and/or intraperitoneal administrations of 5-ALA butyl ester are made, followed one hour later by lamp irradiation. ♦ Control; ■ $AlPcS_4$ 5 mg/kg; × $AlPcS_4$ 1 mg/kg; ✕ 5-ALA butyl ester 338 mg/kg; ∆ 5-ALA butyl ester 338 mg/kg and $AlPcS_4$ 1 mg/kg. The abscissa shows days after treatment; ordinate shows relative tumour volume;

FIG. 7 is as FIG. 1 in which intravenous injections of $AlPcS_{2a}$ and/or intraperitoneal administration of 5-ALA butyl ester are made, followed 1 hour later by lamp irradiation. ▲ Control; ■ $AlPcS_{2a}$ 1 mg/kg; × 5-ALA butyl ester 338 mg/kg; ♦ 5-ALA butyl ester 338 mg/kg and $AlPcS_{2a}$ 1 mg/kg. The abscissa shows days after treatment; ordinate shows relative tumour volume;

FIG. 8 is as FIG. 1 in which intravenous injections of $AlPcS_4$ and/or intraperitoneal administrations of 5-ALA methyl ester are made, followed one hour later by lamp irradiation. ■ Control; ▲ $AlPcS_4$ 1 mg/kg; × 5-ALA methyl ester 273 mg/kg; ♦ 5-ALA methyl ester 273 mg/kg and $AlPcS_4$ 1 mg/kg. The abscissa shows days after treatment; ordinate shows relative tumour volume.

EXAMPLE 1

Formulations 1.1 ALA-containing Cream for Topical Administration

An ALA-containing cream, containing 5–30% ALA, is prepared by admixing ALA with a commercially available cream base.

A 20% ALA cream was prepared by admixture with "Urguentum Merck" cream base (available from Merck) consisting of silicon dioxide, paraffin liq., vaseline, album, cetostearol., polysorbat. 40, glycerol monostearate, Miglyol®812 (a mixture of plant fatty acids), polypropyleneglycol., and purified water.

1.2 ALA for Systemic Administration

For oral administration, ALA is dissolved in acidic soft drinks. For intravenous administration ALA is dissolved in isotonic saline.

1.3 PHOTOFRIN® vascular stroma-localizing photosensitizer for systemic administration PHOTOFRIN® for systemic administration is dissolved in 5% glucose solution.

EXAMPLE 2

PDT using ALA+PHOTOFRIN® vascular stroma-localizing photosensitizer

Materials and Methods

Chemicals 5-aminolevulinic acid (ALA) hydrochloride was purchased from Sigma Chemical Company (St. Louis, Mo.). ALA was freshly dissolved in isotonic saline and given intraperitoneally to mice. PHOTOFRIN® vascular stroma-localizing photosensitizer was obtained from Quadra Logic Technologies (Vancouver, Canada). The solution of PHOTOFRIN® vascular stroma-localizing photosensitizer was made up in isotonic solution containing 5% dextrose and given to mice intravenously via the tail vein.

Animals and Tumor Line

Female Balb/c nu/nu nude mice were obtained from The Animal Department, The Norwegian Radium Hospital, housed 10 per cage and kept under specific-pathogen-free conditions. The mice were 6 weeks old and weighed 20–22 g when the experiments started. The WiDr human colonic carcinoma, used in the present study, was propagated by serial transplantation into the nude mice. Non-necrotic tumor material for inoculation was obtained by sterile dissection of large flange tumors from syngeneic mice. Macroscopically viable tumor tissue was gently minced with a pair of scissors and forced repeatedly through sterile needles of diminishing sizes from 19-gauge to 25-gauge to make a tumor-tissue suspension, 0.02 ml of which was then injected into the dorsal side of the right hind foot of each mouse. The rate of successful transplantations was nearly 100% in the present experiments. No spontaneous necrosis was observed in the tumors which grew to reach 5–7 mm (about 14 days after inoculation) transverse diameter on the day of treatment, as measured with calipers every second day. The tumor volume was calculated using the following formula:

$$V = \pi/6 (D_1 \times D_2 \times D_3)$$

where $D_1$, $D_2$ and $D_3$ are three orthogonal diameters of the tumors which were measured daily by a caliper.

Light Exposure

Unanesthetized mice were fixed in Lucite jigs specially designed for irradiation. The tumor area was exposed to red light from a dicyanomethylane-2-methyl-6-(p-dimethylaminostyryl)-4 H-pyran (DCM) dye laser pumped by a 5W argon ion laser (Spectra Physics, 164). The tuning range was 610–690 nm. The dye laser was tuned at 632 for both ALA-derived PpIX and PHOTOFRIN®vascular stroma-localizing photosensitizer, the tuning being controlled by means of a monochromator. The laser beam was defocused by means of a microscopic ocular. The light was delivered at a fluence rate of 150 mW/cm² for 15-min exposure. The fluence rate of the light on the tumor area was regularly controlled by a calibrated integrating sphere with a photodiode coupled to a digital multimeter (Keithley Instruments, Germany) before and immediately after light illumination.

PDT Efficiency Using ALA or PHOTOFRIN® vascular stroma-localizing photosensitizer Alone, or a Combination of ALA with PHOTOFRIN®

Mice with tumors of the appropriate size were divided into 5 groups (at least 3 animals for each group): group 1 (controls), mice were given neither ALA, PHOTOFRIN® vascular stroma-localizing nor light, only intraperitoneal administration of 0.1 ml saline; group 2 (control-light only) the tumours were irradiated at the same doses as those for groups receiving PDT treatment; group 3 (ALA alone), mice were given an intraperitoneal injection of ALA of 250 mg/kg body weight, followed, 3 hours later, by light exposure as described above; group 4 (PHOTOFRIN® vascular stroma-localizing photosensitizer alone), mice were given an intravenous injection of PHOTOFRIN® vascular stroma-localizing photosensitizer of 1 mg/kg body weight, followed, 3 hours later, by light irradiation; group 5 (ALA and PHOTOFRIN®vascular stroma-localizing photosensitizer), mice were given an intraperitoneal injection of 250 mg/kg ALA and an intravenous injection of 1 mg/kg PHOTOFRIN®vascular stroma-localizing photosensitizer, the tumors were exposed to light 3 hours for both-ALA and PHOTOFRIN®vascular stroma-localizing photosensitizer. Responses of the treated tumors were evaluated as tumor regression/regrowth time. The size of the tumors were measured every day and when the treated tumors reached a volume 5 times that of the volume on the day just before light irradiation, the mice were sacrificed. The data based on the measurements on tumor volumes from each group were pooled to represent mean tumor growth curves.

Results

The growth of the tumors exposed to light 3 hours after an intraperitoneal injection of ALA or an intravenous administration of PHOTOFRIN® vascular stroma-localizing photosensitizer alone or both ALA and PHOTOFRIN® vascular stroma-localizing photosensitizer is shown in FIG. 1. The control tumors (neither drug nor light) grew exponentially with a doubling time of about 5 days. Laser light given to tumors of mice receiving ALA had an effect on the tumor growth. No effect was seen after PDT with PHOTOFRIN® vascular stroma-localizing photosensitizer alone at a dose of 1 mg/kg, a dose that does not induce any skin phototoxicity (data not shown). PDT with a combination of ALA (250 mg/kg) and PHOTOFRIN® vascular stroma-localizing photosensitizer (1 mg/kg) inhibited the growth of the tumors more efficiently than did PDT using ALA (250 mg/kg) alone.

EXAMPLE 3

PDT using ALA+m-THPC

PDT was performed essentially as described in Example 2 using the following groups of animals, with at least 3 animals per group: group 1 (control), mice were given neither ALA (m-THPC) nor light, only intraperitoneal administration of 0.1 ml saline; group 2 (light only), tumors were irradiated with light at the same doses as those for groups of PDT treatment; group 3 (ALA alone), mice were given an intraperitoneal injection of ALA of 250 mg/kg body weight, followed, 3 hours later, by light exposure (632 nm) as described earlier; group 4 (m-THPC alone), mice were given an intravenous injection of m-THPC of 75 µg/kg body weight (a dose that does not induce any skin phototoxicity), followed, 3 hours later, by light irradiation (652 nm); group 5 (ALA and m-THPC), mice were given an intraperitoneal injection of 250 mg/kg ALA and an intravenous injection of 75 µg/kg m-THPC, the tumours were exposed to light (at respective wavelengths) 3 hours for both ALA and m-THPC. Responses of the treated tumors were evaluated as described previously.

Results

FIG. 2 shows that the control tumors (neither drug nor light) grew exponentially with a doubling time of about 5 days. Laser light given to tumors of mice receiving only ALA had an effect on the tumor growth, but no effect was seen after PDT with m-THPC at a dose of 75 µg/kg. PDT with a combination of ALA (250 mg/kg) and m-THPC (75 µg/kg) synergistically enhanced the effect on inhibiting the tumor growth.

EXAMPLE 4

Distribution of ALA and PHOTOFRIN® vascular stroma-localizing photosensitizer

Methods

Human rectal papillary villous adenomas from 2 patients with severe dysplasia and with a diarrheal history for some months before diagnosis were sampled 44 hours after intravenous injection of 2 mg/kg body weight PHOTOFRIN® vascular stroma-localizing photosensitizer or 4.5 hours after oral administration of 60 mg/kg ALA. The samples were immediately immersed in liquid nitrogen, then mounted in medium (Tissue Tek II embedding compound: BDH, Poole, UK). Frozen tissue sections were cut with a cryostat to a thickness of 8 Am and mounted on clean glass slides. The fluorescence localization patterns of ALA-induced PpIX and PHOTOFRIN were studied by fluorescence microscopy. The fluorescence microscopy was carried out with an Axioplan microscope (Zeiss, Germany). The filter combination comprised a 390–440 nm excitation filter, a 460 nm beam splitter and a >600 nm emission filter. The fluorescence images were recorded by a CCD camera (Astromed CCD 3200, Cambridge, UK) and an image processing unit (Astromed/Visilog, PC 486DX2 66 MHz VL).

Results

The results are shown in FIG. 3 for the localization of PHOTOFRIN® vascular stroma-localizing photosensitizer (A) and ALA (B). The adenoma in (A) was from a male patient aged 75, and in (B), a female patient aged 87. Fluorescence of PHOTOFRIN® vascular stroma-localizing photosensitizer is mainly distributed in the stroma of the tumor tissue, whereas the fluorescence of ALA-induced prophyrins is almost entirely localized within the tumor cells.

EXAMPLE 5

Materials and Methods

Chemicals

5-ALA, 5-ALA methyl ester and 5-ALA butyl ester were manufactured by Norsk Hydro Research Center, Porsgrunn, Norway.

5-ALA (ALA) and ALA-Methyl ester (ME) were dissolved in isotonic saline to a final concentration of 0.375 mM.

ALA-Butyl ester (BU) was dissolved in a small amouont of ethanol and diluted further in isotonic saline to a final concentration of 0.375 mM (final ethanol concentration was 2% v/v).

Aluminium phthalocyanine di-sulfonate ($AlPcS_{2a}$) (Porphyrin Products Inc.) dissolved in a few drops of 1M NaOH and diluted in phosphate buffered saline (PBS, 10 MM Na-phosphate pH 7.4/150 mM NaCl) to a final concentration of 0.25 mg/ml.

Aluminium phthalocyanine tetra-sulfonate ($AlPcS_4$) (Porphyrin Products Inc.) dissolved in PBS to a final concentration of 0.25 g/ml, or to 1.25 mg/ml for the high dose experiment in Example 5.3.

PHOTOFRIN ® vascular stroma-localizing photosensitizer (Quadra Logic Technologies) was dissolved in 5% glucose in $H_2O$ to a final concentration of 0.25 mg/ml.

Chlorin e6 (e6)(Porphyrin Products Inc.) was dissolved in PBS to a final concentration of 0.25 mg/ml.

ALA, ALA methyl ester or ALA butyl ester were administered intraperitoneally (i.p.), whereas the sensitizers were injected intravenously (i.v.).

Animals

The animals used were as described in Example 2.

All animals received the same amount of ALA (1.5 mmole), either as the free acid or in the form of an ester. Due to differences in the molecular weights between ALA and the esters, the animals received 250 mg/kg ALA, 278 mg/kg ALA methyl ester and 338 mg/kg of ALA butyl ester.

Experimental

Suspensions of the human tumour (Colon carcinoma WiDr-propagated by serial transplantation) was prepared from non-necrotic areas of the respective tumours and injected (20 µl) into the right hind foot of each mouse. When the tumors have reached a diameter of 5–7 mm, each mouse was injected with the drugs and controls as specified, in Examples 5.1 through 5.5. Injection volume: 100 µl per mouse (approx. 25 g bodyweight).

Illumination occurred one hour after injection of the drugs instead of three hours that was used in previous examples. In contrast to previous examples, a broad-band lamp that covers the range of 600 to 700 nm (Curelight, patent applied for by PhotoCure AS) was used instead of the laser. This was because the light should cover combinations of phthalocyanines (absorption maximum 670 nm) and protoporphyrin IX (absorption maximum 630 nm) induced by ALA or ALA-esters, respectively.

However, the lamp produces light with a lower intensity than the laser. Thus, combinations of ALA and PHOTOFRIN vascular stroma-localizing photosensitizer that were effective in the previous examples when the laser was used will no longer be effective when the lamp is used. This illumination time is optimal for obtaining a vascular effect for most sensitizers and optimal for the esters of ALA but sub-optimal for ALA.

The average tumour volume in each group (mean ±SD) was calculated and plotted against time. The experiment was terminated when the tumor volume had reached 4–5 times the initial volume.

EXAMPLE 5.1

ALA with chlorin e6

Mice with tumours of the appropriate size were divided into three groups of 4–5 mice.

| Group 1: | Control (100 µl physiological saline i.p.) |
| Group 2: | 5-ALA 250 mg/kg (1.5 mmole) i.p. + Chlorin e6 (1 mg/kg) i.v. |
| Group 3: | 5-ALA 250 mg/kg (1.5 mmole) i.p. |
| Group 4: | Chlorin e6 (1 mg/kg) i.v. |

One hour after injection of the drugs the mice were irradiated using the Curelight broad-band lamp (161 mW/cm$^2$ for 15 minutes-144.9 J/cm$^2$).

Responses of the tumors were evaluated as regression/regrowth time. The size of the tumours were measured every second day and the tumour volumes calculated according to the formula in Example 2. The mice were sacrificed when the tumour volume had reached 5 times the initial volume. For each time point, the mean (and the standard deviation of the mean) tumour volume (n=4–5) were calculated. The data were then submitted to statistical analysis (Q-test/90% confidence interval) and extreme values were rejected. The standard deviations were in the majority of cases ≦1.

Results

The results are shown in FIG. 4. Standard deviation bars have been omitted for clarity. It can be seen from the figure that the control tumors reached 4× initial volume within 10 days, and that the control tumors displayed a logarithmic growth. Furthermore, ALA and chlorin e6 when used alone had no effect at the doses used. However, the combination of ALA and chlorin e6 delayed tumor growth significantly. In fact, it took 39 days for the tumor that had been treated with the combination to reach 4 times the initial volume.

EXAMPLE 5.2

ALA methyl ester with AlPcS$_{2a}$

Mice with tumours of the appropriate size were divided into three groups of 4–5 mice.

| Group 1: | Control (100 µl physiological saline i.p.) |
| Group 2: | AlPcS$_{2a}$ (1 mg/kg) i.v. |
| Group 3: | ALA-methyl ester (273 mg/kg) (1.5 mmole) i.p. |
| Group 4: | ALA-methyl ester (273 mg/kg) (1.5 mmole) i.p. + AlPcS$_{2a}$ (1 mg/kg) i.v. |

Mice were irradiated one hour after injection and responses of tumours were evaluated as regression/regrowth time according to Example 5.1.

Results

The results are shown in FIG. 5. It can be seen from the figure that the control tumours reached 4× initial volume in 10 days, and that the control tumours displayed logarithmic growth. ALA-methyl ester had no anti-tumour effect at the dose used, whereas the AlPcS$_{2a}$ displayed a slight effect. Surprisingly, the combination (ALA methyl ester+AlPcS$_{2a}$) resulted in a massive effect. In fact, the tumour volumes did not increase significantly during as long as 40 days after treatment.

EXAMPLE 5.3

ALA Butyl ester with AlPcS$_4$

Mice with tumors of the appropriate size were divided into five groups of 4–5 mice.

| Group 1: | Control (100 µl 2% ethanol i.p.) |
| Group 2: | 5-ALA Butyl-ester 338 mg/kg (1.5 mmole) i.p. + AlPcS$_4$ (1 mg/kg) i.v. |
| Group 3: | AlPcS$_4$ (5 mg/kg) i.v. |
| Group 4: | AlPcS$_4$ (1 mg/kg) i.v. |
| Group 5: | 5-ALA Butyl-ester 338 mg/kg (1.5 mmole) i.p. |

The ethanol was used as the control treatment since the ALA butyl ester formulation contained approx. 2% of ethanol. Mice were irradiated one hour after injection and responses of the tumours were evaluated as regression/regrowth time according to Example 5.1.

Results

The results are shown in FIG. 6. It can be seen from the figure that the control tumours (2% ethanol) and the tumors that were treated with ALA butyl ester reached 4 times the initial volume in 9 and 11 days, respectively. It is also seen that the control tumours grew logarithmically. AlPcS$_4$ (1 mg/kg) is seen to have a moderate effect on tumour growth. However, the tumours that were treated with the combination of ALA butyl ester and AlPcS$_4$ showed a strongly delayed growth, almost identical to that obtained with the high dose of AlPcS$_4$ (5 mg/kg). However, the use of the high dose AlPcS$_4$ resulted in a development of a large oedema. By use of the combination, the anti-tumour effect was the same as for the high dose AlPcS$_4$, whereas the initial oedema was strongly reduced.

EXAMPLE 5.4

ALA Butyl Ester with AlPcS$_{2a}$

Mice with tumours of the appropriate size were divided into three groups of 4–5 mice.

| Group 1: | Control (100 μl physiological saline i.p.) |
| Group 2: | 5-ALA Butyl-ester 338 mg/kg (1.5 mmole) i.p. + AlPcS$_2$ (1 mg/kg) i.v. |
| Group 3: | AlPcS$_2$ (1 mg/kg) i.v. |
| Group 4: | 5-ALA Butyl-ester 338 mg/kg (1.5 mmole) i.p. |

The mice were irradiated one hour after injection and responses of tumours were evaluated as regression/regrowth time according to Example 5.1.

Results

The results are shown in FIG. 7. It can be seen from the figure that the control tumours reached 4× initial volume in 10 days, and that the tumours grew logarithmically. As seen before, the butyl ester had almost no effect on the tumours, whereas the AlPcS$_{2a}$ had an immediate effect (4× volume within 14 days). Again the combination significantly delayed tumour growth, resulting in a slow regrowth; it is seen (after extrapolation) that 4× initial volume will be reached in approximately 30 days.

EXAMPLE 5.5

ALA Methyl Ester with AlPcS$_4$

Mice with tumours of the appropriate size were divided into three groups of 4–5 mice.

| Group 1: | Control (100 μl physiological saline i.p.) |
| Group 2: | 5-ALA methyl ester 273 mg/kg (1.5 mmole) i.p. + AlPcS$_4$ (1 mg/kg) i.v. |
| Group 3: | 5-ALA methyl ester 273 mg/kg (1.5 mmole) i.p. |
| Group 4: | AlPcS$_4$ (1 mg/kg) i.v. |

Mice were irradiated one hour after injection and responses of the tumours were evaluated as regression/regrowth time according to Example 5.1.

Results

The results are shown in FIG. 8. It can be seen from the figure that the control tumours reached 4 times the initial volume in 10 days, and the growth of the control tumours occurred in a logarithmic manner. As seen before, the methyl ester did not have any effect on tumor growth, whereas the AlPcS$_4$ had an intermediate effect. Strikingly, the combination of the ALA methyl ester+AlPcS$_4$ resulted initially in a substantial reduction of tumour volume followed by a slow regrowth of the tumour. In fact, this is the only combination that actually resulted in an initial loss of tumour size. The tumour reached 4 times the initial volume at approx. 35 days.

What is claimed is:

1. A method for the treatment of disorders or abnormalities of internal surfaces of the body which are responsive to photochemotherapy, said method comprising simultaneous, separate or sequential administration to affected surfaces of the body of a protoporphyrin precursor photochemotherapeutic agent and a vascular stroma-localizing photosensitizer, and optionally at least one chelating agent, wherein the photochemotherapeutic agent and photosensitizer have a syncrgistically enhanced therapeutic efficacy relative to the photochemotherapeutic agent or photosensitizer alone, and wherein the total dosage of the vascular stroma-localizing photosensitizer administered is in the range of 0.01 to 10 mg/kg body weight and the total dosage of the protoporphyrin precursor photochemotherapeutic agent administered is in the range of 1 to 500 mg/kg body weight, and exposing the surfaces to light.

2. The method of claim 1, wherein the light is in the wavelength region 350–900 nm.

3. The method of claim 1, wherein the total dosage of the vascular stroma-localizing photosensitizer administered is in the range of 0.01 to 1 mg/kg body weight and the total dosage of the protopophyrin precursor photochemotherapeutic agent is in the range of 1 to 500 mg/kg body weight.

* * * * *